(12) United States Patent
Oesterhelt et al.

(10) Patent No.: US 7,939,220 B2
(45) Date of Patent: May 10, 2011

(54) PROTON-TRANSLOCATING RETINAL PROTEIN

(75) Inventors: Dieter Oesterhelt, München (DE); Norbert Hampp, Amöneburg-Rossdorf (DE); Matthias Pfeiffer, Marburg (DE)

(73) Assignee: Mib Munich Innovative Biomaterials GmbH, Martinsried (DE)

( * ) Notice: Subject to any disclaimer, the term of this patent is extended or adjusted under 35 U.S.C. 154(b) by 110 days.

(21) Appl. No.: 10/343,318

(22) PCT Filed: Jul. 27, 2001

(86) PCT No.: PCT/EP01/08715
§ 371 (c)(1),
(2), (4) Date: Sep. 8, 2003

(87) PCT Pub. No.: WO02/10207
PCT Pub. Date: Feb. 7, 2002

(65) Prior Publication Data
US 2004/0054141 A1    Mar. 18, 2004

(30) Foreign Application Priority Data

Jul. 27, 2000  (DE) ................. 100 36 745
Sep. 29, 2000  (DE) ................. 100 48 383

(51) Int. Cl.
*G03H 1/18* (2006.01)
*C07K 4/04* (2006.01)
*C07K 14/215* (2006.01)

(52) U.S. Cl. ............. 430/1; 430/2; 359/3; 365/125; 365/121; 530/350

(58) Field of Classification Search .......... None
See application file for complete search history.

(56) References Cited

U.S. PATENT DOCUMENTS 6,274,279 B1 * 8/2001 Hampp et al. ............ 430/1

FOREIGN PATENT DOCUMENTS

WO    WO 94/05008    3/1994

OTHER PUBLICATIONS

Delaney, John K., and Subramaniam Sriram. (1996) Biophysical Journal, 70, 2366-2372.*
Tittor, J., Schweiger, U., Oesterhelt, D., and Bamberg, E. (1994) Biophysical Journal, 67, 1682-1690.*
Merriam-Webster OnLine reference.*
Greenhalgh, D.A., et al. 1993 Journal Biol Chem 268(27): 20305-20311.*
Krebs, M.P., et al. 1993 Journal of Bacteriology 175(6): 1555-1560.*
Luecke, H., et al. 1999 Science 286: 255-260.*
Delaney, J. et al., "The Residues Leu 93 and Asp 96 Act Independently in the Bacteriorhodopsin Photocyte: Studies with the Leu 93→Ala, Asp 96→Asn Double Mutant," *Biophysical Journal* 70(5):2366-2372, May 1996.
Oesterhelt, D. et al., "Bacteriorhodopsin : A Biological Material for Information Processing," *Quarterly Reviews of Biophysics* 24(4):425-478, 1991.
Barnidge, D., et al., "Extraction Method for Analysis of Detergent-Solubilized Bacteriorhodopsin and Hydrophobic Peptides by Electrospray Ionization Mass Spectrometry," *Analytical Biochemistry*, 269:1-9, 1999.
Hufnagel, P., et al., "Electrospray Ionization Mass Spectrometry of Genetically and Chemically Modified Bacteriorhodopsins," *Analytical Biochemistry*, 243:46-54, 1996.
Oesterhelt, D., et al., "Reconstitution of Bacteriorhodopsin," *FEBS Letters*, 44(3):262-265, Aug. 1974.
Oesterhelt, D., et al., "Light-Dependent Reaction of Bacteriorhodopsin with hydroxylamine in Cell Suspensions of *Halobacterium halobium*: Demonstration of an Apo-Membrane," *FEBS Letters*, 44(3):257-261, Aug. 1974.
Ihara et al., "Met-145 Is a Key Residue in the Dark Adaptation of Bacteriorhodopsin Homologs" Biophysical Journal 67:1187-1191, 1994.

* cited by examiner

*Primary Examiner* — David J Steadman
*Assistant Examiner* — Marsha M Tsay
(74) *Attorney, Agent, or Firm* — Seed IP Law Group PLLC

(57) ABSTRACT

The invention relates to proton-translocating retinal proteins which exhibit a photocycle which is retarded as compared with the wild type and whose all-trans retinal contents in the light-adapted and dark-adapted states do not differ from each other by more than 10%. The invention furthermore relates to a photochromic composition and to the use of the proton-translocating retinal proteins and the photochromic composition.

10 Claims, 4 Drawing Sheets

SEQUENCE LISTING

```
<160> NUMBER OF SEQ ID NOS: 1

<210> SEQ ID NO 1
<211> LENGTH: 248
<212> TYPE: PRT
<213> ORGANISM: Halobacterium salinarum

<400> SEQUENCE: 1

Glu Ala Gln Ile Thr Gly Arg Pro Glu Trp Ile Trp Leu Ala Leu Gly
 1               5                  10                  15

Thr Ala Leu Met Gly Leu Gly Thr Leu Tyr Phe Leu Val Lys Gly Met
                20                  25                  30

Gly Val Ser Asp Pro Asp Ala Lys Lys Phe Tyr Ala Ile Thr Thr Leu
            35                  40                  45

Val Pro Ala Ile Ala Phe Thr Met Tyr Leu Ser Met Leu Leu Gly Tyr
    50                  55                  60

Gly Leu Thr Met Val Pro Phe Gly Gly Glu Gln Asn Pro Ile Tyr Trp
65                  70                  75                  80

Ala Arg Tyr Ala Asp Trp Leu Phe Thr Thr Pro Leu Leu Leu Leu Asp
                85                  90                  95

Leu Ala Leu Leu Val Asp Ala Asp Gln Gly Thr Ile Leu Ala Leu Val
            100                 105                 110

Gly Ala Asp Gly Ile Met Ile Gly Thr Gly Leu Val Gly Ala Leu Thr
        115                 120                 125

Lys Val Tyr Ser Tyr Arg Phe Val Trp Trp Ala Ile Ser Thr Ala Ala
    130                 135                 140

Met Leu Tyr Ile Leu Tyr Val Leu Phe Phe Gly Phe Thr Ser Lys Ala
145                 150                 155                 160

Glu Ser Met Arg Pro Glu Val Ala Ser Thr Phe Lys Val Leu Arg Asn
                165                 170                 175

Val Thr Val Val Leu Trp Ser Ala Tyr Pro Val Val Trp Leu Ile Gly
            180                 185                 190

Ser Glu Gly Ala Gly Ile Val Pro Leu Asn Ile Glu Thr Leu Leu Phe
        195                 200                 205

Met Val Leu Asp Val Ser Ala Lys Val Gly Phe Gly Leu Ile Leu Leu
    210                 215                 220

Arg Ser Arg Ala Ile Phe Gly Glu Ala Glu Ala Pro Glu Pro Ser Ala
225                 230                 235                 240

Gly Asp Gly Ala Ala Ala Thr Ser
                245
```

PROTON-TRANSLOCATING RETINAL PROTEIN

CROSS-REFERENCES TO RELATED APPLICATIONS

This application is a U.S. National Stage filing of PCT Application No. PCT/EP01/008715, international filing date of Jul. 27, 2001; which claims priority to German Application No. 100 36 745.3 filed Jul. 27, 2000 and German Application No. 100 48 383.6 filed Sep. 29, 2000; all of these applications are incorporated herein by reference in their entireties.

The invention relates to a protein-translocating retinal protein, to a photochromic composition which comprises the proton-translocating retinal protein and to the use of the proton-translocating retinal protein and the composition.

Halobacteria are Archaea, which, alongside the Bacteria and Eukarya, form a third domain of life. Archaea owe their name to the unusual biotopes in which they are found. They frequently live under "archaic" conditions, i.e. at extreme temperatures, salt concentrations or pH values as may have prevailed on the early surface of the earth.

The halophilic Archaea comprise 9 genera (e.g. *Halobacterium, Haloferax, Natronomonas*, etc.) and are without exception extremophilic, i.e. they live in salt solutions whose concentrations extend from 2 molar to saturation and which sometimes additionally exhibit alkaline pH values of up to pH 11. In nature, the Halobacteria are part of a complex ecosystem. After the annual downpours, the salinity in salt-producing installations, which otherwise increases in association with permanent insolation, or the conditions in the Dead Sea and other natural hypersaline bodies of water, initially permit the photolithotrophic growth of the halotolerant green alga *Duniella parva* up to a salt content of about 12%. After the conditions which are optimal for it have been exceeded, *Duniella* dies and makes possible the massive growth of halophilic Archaea which, due to their carotenoid content, frequently lead to these bodies of water becoming red in color.

Aside from fermentation and aerobic and anaerobic respiration, the halophilic Archaea possess an additional option, which is unique among the Archaea, for converting energy: they are able to take up and convert energy by means of retinal-dependent photosynthesis. In contrast to the green, chlorophyll-dependent photosynthesis, only one single protein is involved in the uptake and conversion of energy in this case, namely a light-driven proton-translocating retinal protein.

The best known example of such a proton-translocating retinal protein is the archaebacterial proton pump bacteriorhodopsin (BR), which uses light energy directly for generating an electrochemical proton gradient which is converted into chemical energy. Bacteriorhodopsin is an intrinsic membrane protein having a molecular weight of approx. 26 kDa. The polypeptide chain traverses the membrane seven times and in this way forms a secondary structure consisting of seven helical transmembrane regions. A retinal (vitamin A aldehyde) is bonded covalently to the side chain of a lysine belonging to the seventh helix in the interior of the protein. The resulting CH=N group is termed a Schiff's base (SB) and, in the initial state, is protonated on the nitrogen (SBH). The article by Haupts et al. (Annu. Rev. Biophys. Biomol. Struct. 28, 367-99, 1999) provides a review of bacteriorhodopsin.

The BR chromophore absorbs yellow-green light maximally at 570 nm, which means that BR appears violet to the human eye. After a photon has been absorbed, the protein undergoes chemical and structural changes which lead to distinguishable, spectroscopically measurable intermediates. They are designated by the letters K, L, M, N and O and are in each case labeled with the wavelength at which absorption is maximal. In a simplified manner, the cycle can be described as follows:

$BR_{570} \rightarrow K_{590} \rightarrow L_{550} \rightarrow M_{410} \rightarrow N_{560} \rightarrow O_{640} \rightarrow BR_{570}$ Bacteriorhodopsin is thus far the only retinal protein which is known to occur in nature in the form of a two-dimensional crystal. In the bacterium, the crystals are located in what is known as the purple membrane. The organization in the purple membrane stabilizes the protein to such an extent that the protein has been proposed for a number of technical applications (summarized in Oesterhelt et al., Quarterly Rev. Biophysics 24, 425-478, 1991). These applications can make use of the changes in the pH of the solution, in electrical potential and in color which occur on illumination.

Thus, the change in color from the violet of the bacteriorhodopsin in the initial state $BR_{570}$ to the yellow in the intermediate state $M_{410}$ is the basis for applications in optical information technology. The decomposition of the intermediate $M_{410}$, which has a lifetime of a few milliseconds, is the rate-determining step in this cycle. The light intensity and the thermal decomposition constant of the M intermediate determine the ratio of the colors violet and yellow in the photocycle.

In the dark, the retinylidene moiety of the bacteriorhodopsin is present as a mixture of all-trans, 15-anti and 13-cis, 15-syn configurations in a ratio of about 60:40. Only the all-trans form of the chromophore mediates the physiological process of proton translocation and passes through the yellow intermediate $M_{410}$ ("trans cycle"). While the absorption of photons in the 13-cis configuration also leads to a cycle of color changes, i.e. the "cis cycle", this latter differs from the "trans cycle" in that no yellow M-like intermediate is formed. On illumination, the molecule jumps, with a very low degree of probability, from the "cis cycle" into the "trans cycle". This change from the "cis cycle" to the "trans cycle" is termed light adaptation of the dark-adapted form. In practice this means that, after a sample has been stored in the dark (dark adaptation), an initial illumination only leads to about 60% of the theoretically possible M intermediate. Further illumination causes the sample to gradually adapt (light adaptation), such that finally all the molecules are transferred to the "trans cycle" and pass through the M intermediate.

The change of the molecules from the "cis cycle" to the "trans cycle" leads to the absorption maximum being shifted by several nm and represents a substantial disadvantage for using bacteriorhodopsins when producing photochromic products, for example optical films or printing inks.

It would, therefore, be desirable to prepare proton-translocating retinal proteins whose absorption maximum in the dark-adapted state corresponded as precisely as possible to that in the light-adapted state. In addition to this, it would be advantageous if it were possible to increase the stability of the M intermediate in order to be able to observe the change in color, from violet to yellow, of the molecules present in the "trans cycle" as precisely as possible.

The invention now provides a proton-translocating retinal protein which is selected from the group of:
(i) muteins of a natural proton-translocating retinal protein derived from halophilic archaebacteria which exhibit a retarded photocycle (type 1 mutation) and whose all-trans retinal contents in the light-adapted and dark-adapted states do not differ from each other by more than 10% (type 2 mutation) and/or (ii) homologs of the muteins (i) which possess a retarded photocycle and whose retinal isomer compositions in the light-adapted and dark-adapted states do not differ from each other by more than 10%.

A mutein is understood as meaning protein-translocated retinal proteins which have been altered by a substitution, deletion or insertion. Muteins can exhibit one or more mutations. In this connection, type 1 mutations are mutations which lead to a retardation of the photocycle as compared with the natural retinal protein derived from *Halobacterium salinarum* (SEQ ID No. 1). In this context, the photocycle is measured as described, for example, by Miller & Oesterhelt, Biochem. Biophys. Acta 1020, 57-64, 1990. Type 2 mutations lead to a constancy in the all-trans retinal content in the light-adapted and dark-adapted protein which is greater than that of the natural retinal protein derived from *Halobacterium salinarum* (SEQ ID No. 1). In this context, the all-trans retinal content is determined as described by Tittor et al., Biophys. J. 67, 1682-1690, 1994. The percentage value refers to the total content of retinal isomers which can be determined using the method mentioned. Normally, type 1 mutations and type 2 mutations affect different amino acids. However, it is also possible for a single mutation to exhibit both the desired effects and therefore to be classified simultaneously as being a type 1 and type 2 mutation. Insofar as naturally occurring, archaebacterial proton-translocating retinal proteins exhibit a photocycle which is retarded as compared with that of the best-known proton-translocating retinal protein, i.e. bacteriorhodopsin derived from *Halobacterium salinarum* (SEQ ID No. 1), and their all-trans retinal contents in the light-adapted and dark-adapted states do not differ from each other by more than 10%, they are likewise regarded as being muteins within the context of the present invention.

The term "homolog", which is known to the skilled person, denotes a relationship between two or more peptides, polypeptides or proteins which can be determined, on the basis of the degree of congruence between the sequences, using known methods, for example computer-assisted sequence comparisons (basic local alignment search tool, S. F. Altschul et al., J. Mol. Biol. 215 (1990), 403-410). The percentage identity is calculated from the percentage of identical regions in two or more sequences while taking into account gaps or other special sequence features. As a rule, use is made of special computer programs which employ algorithms which take the particular requirements into account.

Preferred methods for determining homology initially generate the greatest degree of congruence between the sequences being investigated. Computer programs for determining the identity between two sequences include, but are not restricted to, the GCG program package, including GAP (Devereux, J., et al., Nucleic Acids Research 12 (12):387 (1984); Genetics Computer Group University of Wisconsin, Madison, (Wis.)); BLASTP, BLASTN and FASTA (Altschul, S. et al., J. Mol. Biol. 215: 403-410) (1999)). The BLASTX program can be obtained from the National Centre for Biotechnology Information (NCBI) and from other sources (BLAST Manual, Altschul S., et al., NCB NLM NIH Bethesda MD 20894; Altschul S., et al., Mol. Biol. 215: 403-410 (1990)). The well-known Smith-Waterman algorithm can also be used for determining the percentage identity.

Preferred parameters for the amino acid sequence comparison comprise the following:

| | |
|---|---|
| Algorithm: | Needleman and Wunsch, J. Mol. Biol. 48: 443-453 (1970) |
| Comparison matrix: | BLOSUM 62 from Henikoff and Henikoff, PNAS USA 89 (1992), 10915-10919 |
| Gap penalty: | 12 |
| Gap length penalty: | 4 |
| Threshold of similarity: | 0 |

The GAP program is also suitable for being used with the abovementioned parameters. The abovementioned parameters are the default parameters for amino acid sequence comparisons in which gaps at the ends do not alter the value. The invention therefore also encompasses fusion proteins, i.e. proton-translocating retinal proteins which possess a fusion protein moiety. When sequences which are very short as compared with the reference sequence are being dealt with, it can furthermore be necessary to increase the expectation value up to a maximum of 100 000 and, where appropriate, to decrease the word size down to a minimum of 2.

It is possible to use other exemplary algorithms, gap opening penalties, gap extension penalties and comparison matrices, including those mentioned in the program manual, Wisconsin package, Version 9, September 1997. The choice will depend on the comparison to be performed and, in addition, whether the comparison is carried out between sequence pairs, in which case GAP or best fit is preferred, or between a sequence and an extensive sequence database, in which case FASTA or BLAST is preferred.

Within the context of this application, a congruence of 40%, as determined using the abovementioned algorithm, is described as being 40% identity. The same applies, in a corresponding manner, to higher percentages.

It has now been found, surprisingly, that combining a type 1 mutation and a type 2 mutation in the proton-translocating retinal protein according to the invention can lead to an extensive degree of constancy in the all-trans retinal content and to a retardation of the photocycle. As a rule, the all-trans retinal content of the dark-adapted form of the proton-translocating retinal protein according to the invention does not differ from that of the light-adapted form by more than 10%. In preferred embodiments, the differences are even smaller and are maximally 8 and even maximally 5%. It has furthermore been found, surprisingly, that it is precisely muteins whose all-trans retinal contents in the light-adapted and dark-adapted states do not differ significantly, i.e. by not more than 10%, which exhibit all-trans retinal contents of at least 60% in both the light-adapted and dark-adapted states. This unexpected side effect is extremely advantageous since any increase in the proportion of molecules which participate in the "trans cycle" leads, on illumination, to a more distinct color change and consequently to an improvement in the optical properties.

The invention provides muteins which exhibit a constant all-trans retinal content in the range from at least 60 to 100%, preferably from 62% or 65% to 100%. Whereas most retinal proteins exhibit an all-trans retinal content in the range from 60 or 65% to 85%, particularly preferred embodiments provide for an all-trans retinal content of at least 70% or 75%, at best even from 80% to 100%.

In a preferred embodiment, the natural proton-translocating retinal protein whose mutein(s) exhibit(s) the abovementioned properties is an archaebacterial bacteriorhodopsin, e.g.

a halobacterial rhodopsin, preferably *Halobacterium salinarum* bacteriorhodopsin (SEQ ID No. 1).

The protein-translocating retinal protein according to the invention encompasses muteins which possess a type 1 mutation and a type 2 mutation and whose amino acid sequence exhibits an identity of at least 40% with the amino acid sequence SEQ ID No. 1. In other embodiments, the identity is at least 50, 60 or 70%. In particularly preferred embodiments, the identity is at least 80, 90 or 95%.

In another preferred embodiment, the proton-translocating retinal protein is a homolog having an amino acid sequence which, in the region of the C helix and/or the F helix, exhibits an identity of at least 60% with the corresponding amino acid sequences of the mature bacteriorhodopsin from SEQ ID No. 1. In other preferred embodiments, the percentage identity in the case of the C helix and/or the F helix is at least 70, 80 or 90%, preferably at least 95%. In this connection, the degree of identity in the case of C helix and the F helix can be the same or different.

The photocycle of the proton-translocating retinal protein according to the invention is retarded by the type 1 mutation. In every case, the thermal cycle time is more than 10 ms, preferably more than 1 s or even more than 10 s. In particularly preferred embodiments, the thermal cycle time is in the region of minutes, i.e. it is more than 1 min and, in other preferred embodiments, even more than 5 or 10 min. While, in the extreme case, the thermal cycle time can be up to 2 hours, it is as a rule not more than 90 or 60 min.

The type 1 mutation of the proton-translocating retinal protein can consist of an amino acid substitution at one or more of the amino acid positions which are involved in the catalytic cycle in the natural protein. The present invention therefore encompasses the retinal proteins in which, for example, one or more of the positions of the amino acids which are involved in the proton translocation, i.e. from the group of the amino acid residues D38, R82, D85, D96, D102, D104, E194 and/or E204 as depicted in SEQ ID No. 1, or the amino acid residues which correspond to them in homologous proteins, is/are altered. A preferred amino acid substitution is D96N, i.e. the amino acid D at position 96 of SEQ ID No. 1, or the corresponding amino acid in a homologous protein, is replaced with N. Other preferred amino acid substitutions are D38R and D102R and/or D104R.

The type 2 mutation of the retinal proteins of the retinal proteins according to the invention leads to an amino acid substitution at one or more of the amino acid positions which form the retinal binding pocket and/or immediately adjacent positions. The retinal binding pocket is understood as meaning the sum of the amino acids which confer on the Schiff's base of the retinal its characteristic chemical and physical properties. The amino acids which form the retinal binding pocket, or immediately adjacent amino acids, are selected from the group of the amino acid residues Val49, Ala53, L93, Met118, Gly122, S141 and Met145 as depicted in SEQ ID No. 1 or the amino acid residues which correspond to them in homologous proteins. In preferred embodiments, the type 2 mutation is V49A, V49G, V49F, L93A, G122K, G122C, G122M, S141A, S141M, M145I, M145F, M145W, M145C or M145K. Surprisingly, these type 2 mutations bring about a constancy in the proportion of all-trans in the retinylidene moiety of the bacteriorhodopsin in the light-adapted and dark-adapted states.

Absorption maxima and retinal isomer ratios of the *Halobacterium salinarum* wild type (WT), of the pure type 1 mutant D96N, of the pure type 2 mutants M145F and L93A and of the retinal proteins according to the invention, i.e. D96N-M145F and D96N-L93A, are shown in the following table:

| | | | Isomers | | | |
| | $\lambda_{max}$ in nm | | DA | | LA | |
| Strain | DA | LA | all-trans | 13-cis | all-trans | 13-cis |
|---|---|---|---|---|---|---|
| WT | 560 | 568 | 60 | 40 | 98 | 2 |
| D96N | 560 | 569 | 54 | 46 | 96 | 4 |
| M145F | 558 | 559 | 72 | 28 | 86 | 14 |
| D96N-M145F | 560 | 560 | 66 | 34 | 67 | 33 |
| L93A | 541 | 541 | 80 | 20 | 82 | 18 |
| D96N-L93A | 544 | 544 | 80 | 20 | 81 | 19 |

Note:
"DA" denotes "dark-adapted"
"LA" denotes "light-adapted"

Examples of particularly preferred combinations of type 1 and type 2 mutations are V49A-D96N, L93A-D96N and M145F-D96N (see FIG. 1).

In another embodiment, the retinal proteins according to the invention are present in membrane-bound form, with the membrane having a density of between 1.10 and 1.20 g/cm$^3$. In a preferred embodiment, the density is between 1.175 and 1.185 g/cm$^3$. Particular preference is given to the form of a purple membrane having a density of 1.18 g/cm$^3$.

The invention furthermore provides nucleic acids which encode the above-described retinal proteins. These nucleic acids can be produced, on the one hand, by mutating previously known genes for proton-translocating retinal proteins, e.g. the gene encoding the *Halobacterium salinarum* bacteriorhodopsin (Dunn et al., Proc. Natl. Acad. Sci. USA 78, 6744-6748, 1981), or, on the other hand, be prepared entirely synthetically using known methods. Since the genetic code of the Archaea does not differ from that of the Prokarya and Eukarya, it is also possible to use the known rules to prepare nucleic acids which are intended to be transformed into halobacteria. However, the skilled person will endeavor to allow for a codon usage which is matched to the host organism which is in each case designated for the purpose. The nucleic acids according to the invention can be ribonucleic acids and/or deoxyribonucleic acids.

The invention furthermore provides vectors which comprise nucleic acids which encode the proton-translocating retinal proteins. Depending on the host organism which is designated for this vector, the skilled person will choose between archaebacterial vectors and vectors for expression in Prokarya (*E. coli, Bacillus, Pseudomonas, Klebsiella*, etc.) or Eukarya (yeast, animal cell cultures (CHO, HeLa, COS, etc.), plants or plant cells and insect cells).

The invention furthermore provides a host cell which contains either a nucleic acid encoding a protein-translocating retinal protein according to the invention or a vector according to the invention. The host cells are, for example, Archaea, preferably halobacteria, particularly preferably *Halobacterium salinarum*, whose transformation has been described (Cline et al., Can. J. Microbial. 35, 148-152, 1989). Alternatively, it is also possible to express vectors according to the invention in *E. coli* or other prokaryotic hosts and, if required, in the abovementioned eukaryotic cells as well.

The invention furthermore provides a photochromic composition which can comprise, in addition to a proton-translocating retinal protein according to the invention, stabilizers, foam formation-diminishing and/or UV light-absorbing additives and/or buffering substances.

The photochromic composition according to the invention can comprise, for example, glycerol, organic polymers and/or organic solvents.

The proton-translocating retinal proteins according to the invention, or the photochromic compositions which comprise them, can be used for producing optical films. The production of optical films from bacteriorhodopsins is already known and is described in detail, for example, in Hampp et al., SPIE 3623, 243, 1999. An optical film which has been produced using the proton-translocating retinal proteins according to the invention is suitable for optical recording. Another possibility of using such optical films is in interferometry or in holographic pattern recognition. It is also possible to use optical films as optical light modulators. In addition to this, it is possible to conceive of producing capacious stores for optical data storage (Birge, Scientific American, 1995, 66).

The present invention furthermore provides the use of a proton-translocating retinal protein and/or a photochromic composition as a security dye. In a first embodiment, the retinal protein and/or the photochromic composition is/are applied to a document which requires security or to an article which requires security. In another embodiment, the photochromic composition according to the invention, or the retinal protein, which is applied to the document which requires security or to the article which requires security can be fixed on the document or the article.

In this connection, the fixing according to the present invention can be affected by physical inclusion or covalent coupling to the document. According to the invention, the document which requires security is, for example, a security paper, a pass or a banknote. However, according to the invention, the document can also be any other document which requires security.

Finally, the present invention provides a process for producing documents which possess security features, which is characterized in that, before, during or after the production of a document in a customary manner, a proton-translocating retinal protein according to the invention or a photochromic composition according to the invention is applied and, where appropriate, fixed to it.

The following figures and examples explain the invention.

FIG. 1 shows the absorption spectra of different proton-translocating retinal proteins according to the invention as compared with the spectra of the wild type or of muteins which possess only one mutation. In each case, the continuous lines show the absorption spectrum in the light-adapted state while the dotted lines show the absorption spectrum in the dark-adapted state. In detail:

Figure 1A:
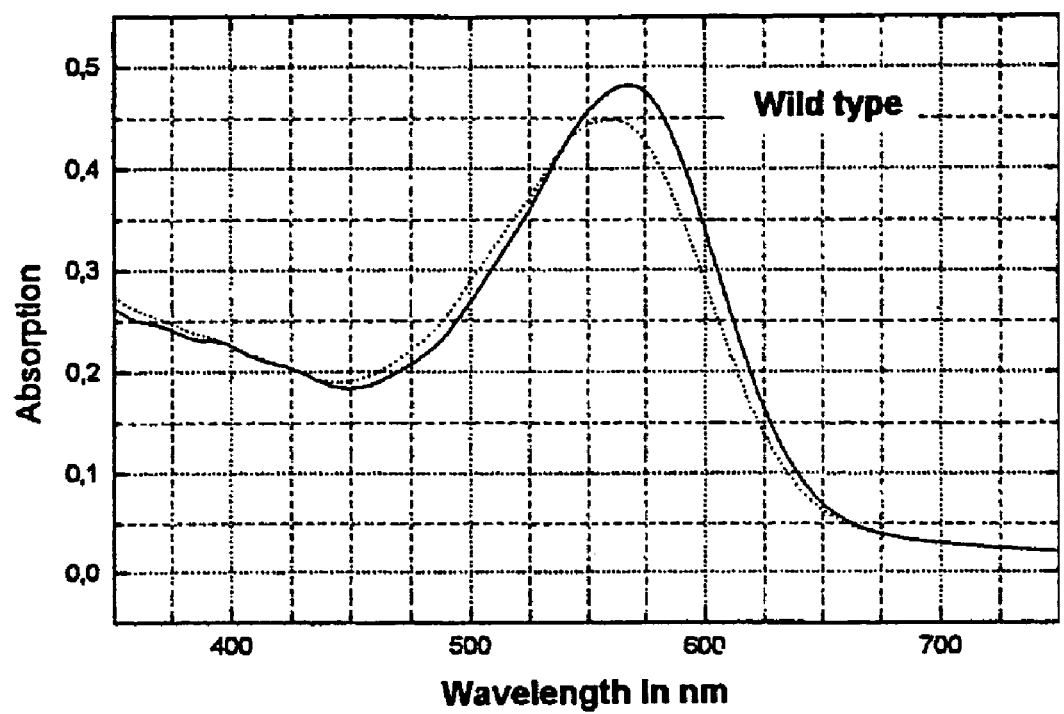
FIG. 1A shows *Halobacterium salinarum* wild type having the amino acid sequence depicted in SEQ ID No. 1. The absorption maximum is 568 nm in the light-adapted state and 560 nm in the dark-adapted state.
Figure 1B:
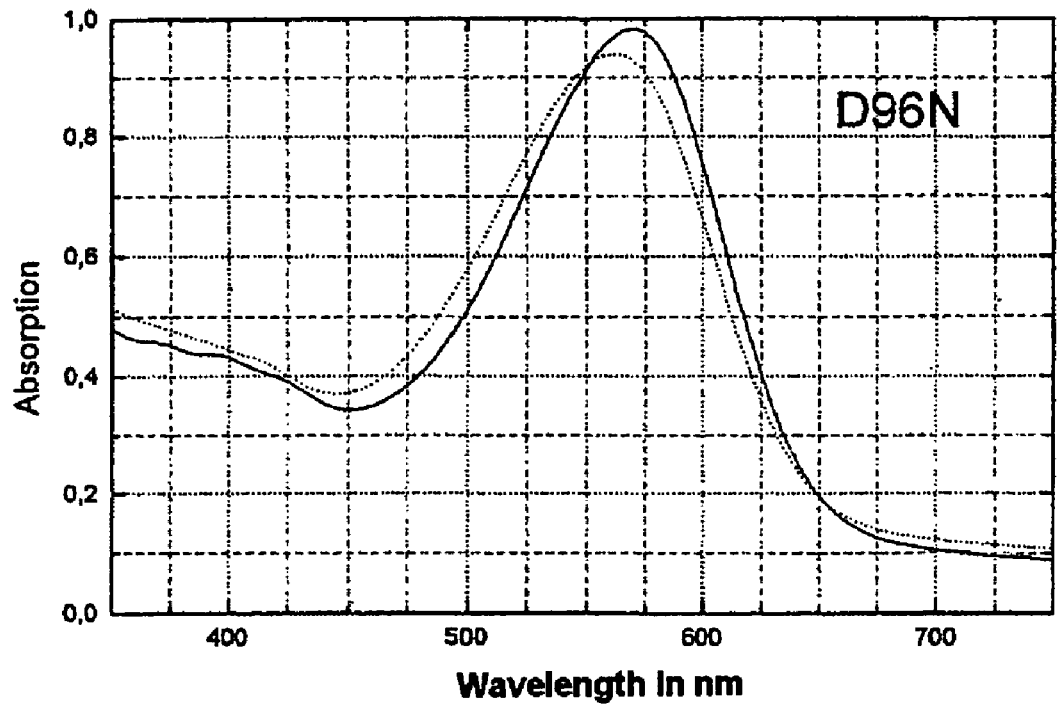
FIG. 1B shows the absorption spectrum of the type 1 mutant D96N. The absorption maximum shifts from 569 nm in the light-adapted state to 560 nm in the dark-adapted state.
Figure 1C:
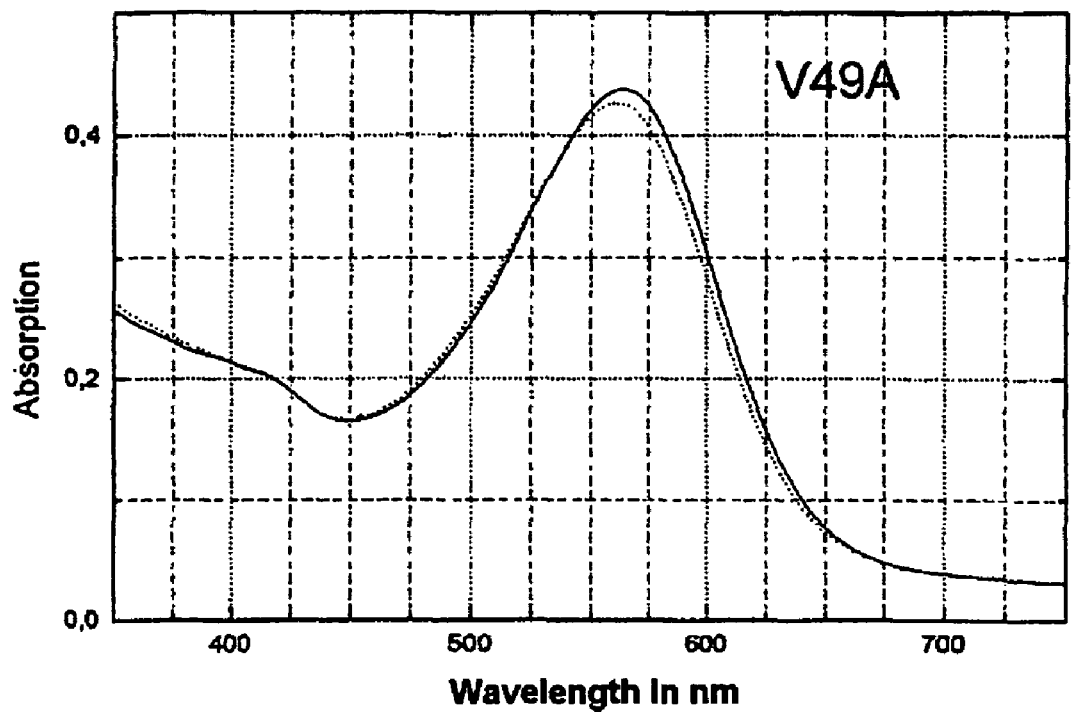
FIG. 1C shows the type 2 mutant V49A. The absorption maximum is 549 nm in both the light-adapted and the dark-adapted states.
Figure 1D:
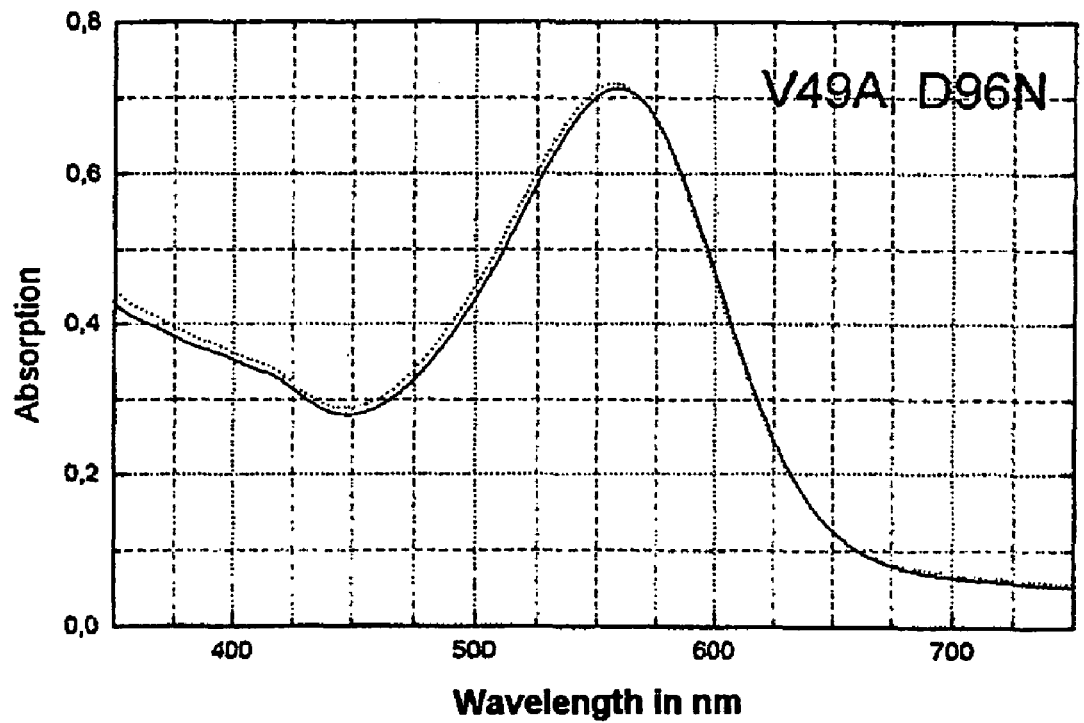
FIG. 1D shows the retinal protein according to the invention having the double mutation V49A-D96N. The absorption maximum of 559 nm in the light-adapted state is displaced by 2 nm, to 557 nm, in the dark-adapted state.
Figure 1E:
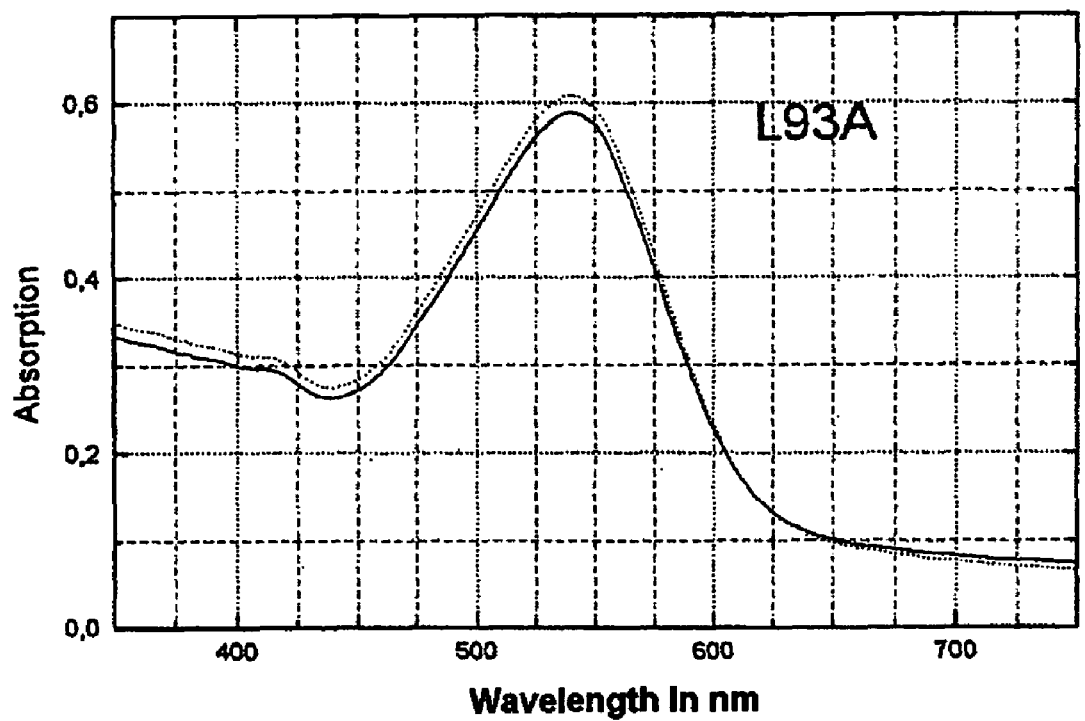
FIG. 1E shows the type 1 mutation L93A. The absorption maximum is 541 nm in both the light-adapted state and the dark-adapted state.
Figure 1F:
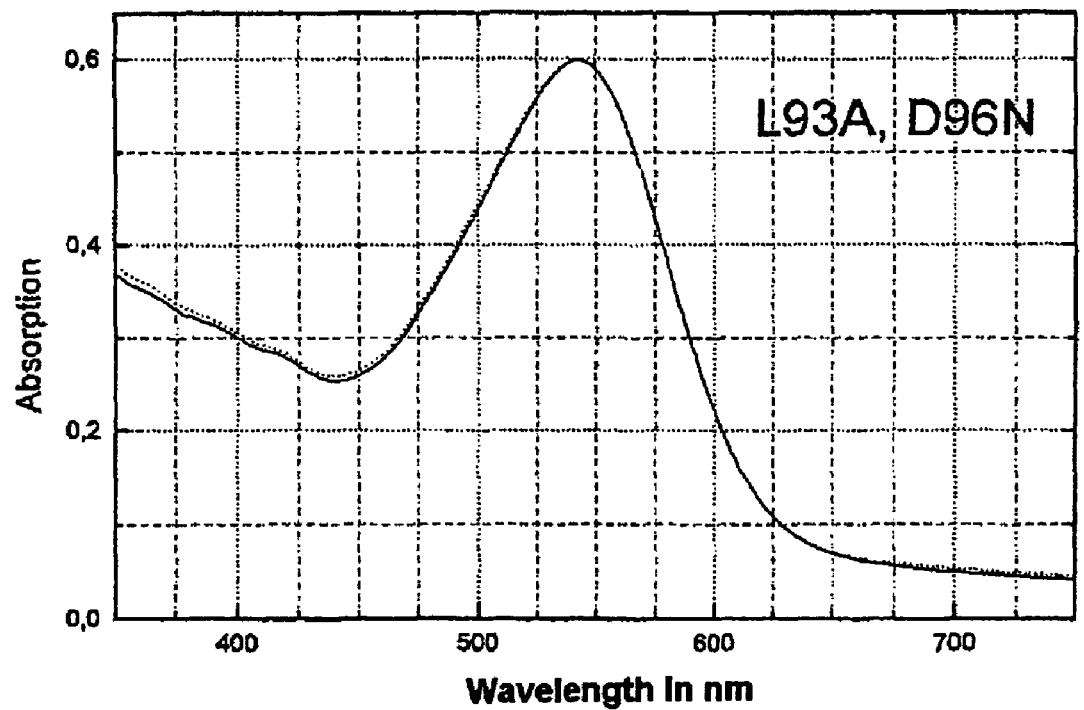

FIG. 1F shows the retinal protein according to the invention having the double mutation L93A-D96N. The absorption maximum is 544 nm in both the light-adapted and dark-adapted states. In the dark-adapted state, this double mutant achieves an all-trans content of more than 80%.

Figure 1G:
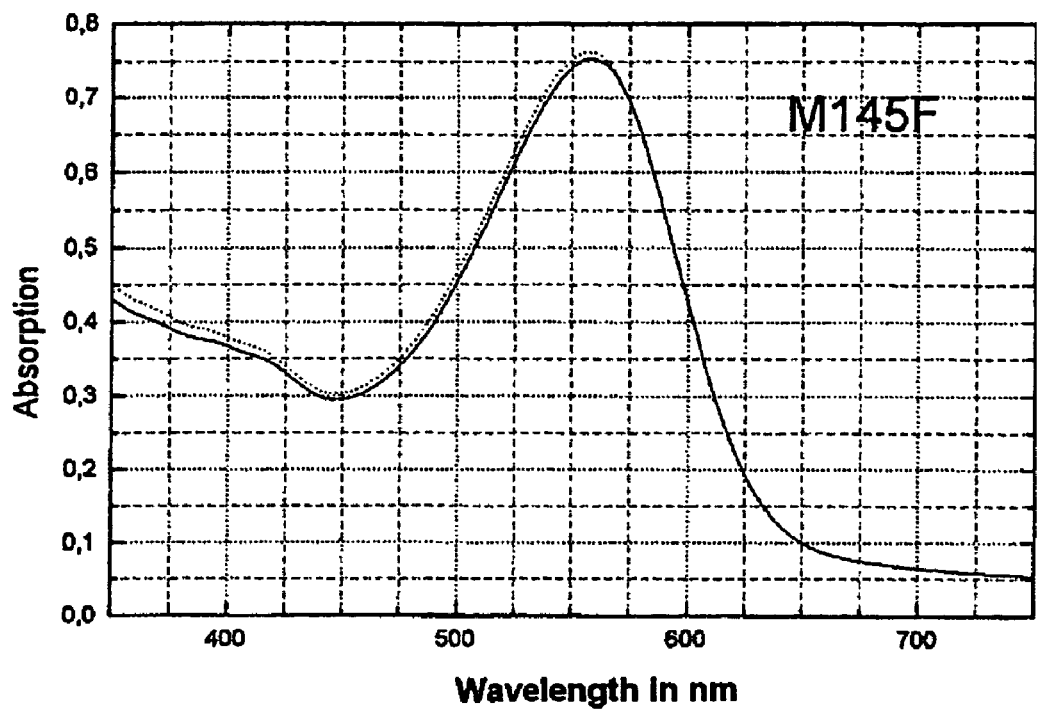

FIG. 1G shows the type 2 mutation M145F. The absorption maximum is 559 nm in the light-adapted state and 558 nm in the dark-adapted state.

Figure 1H:
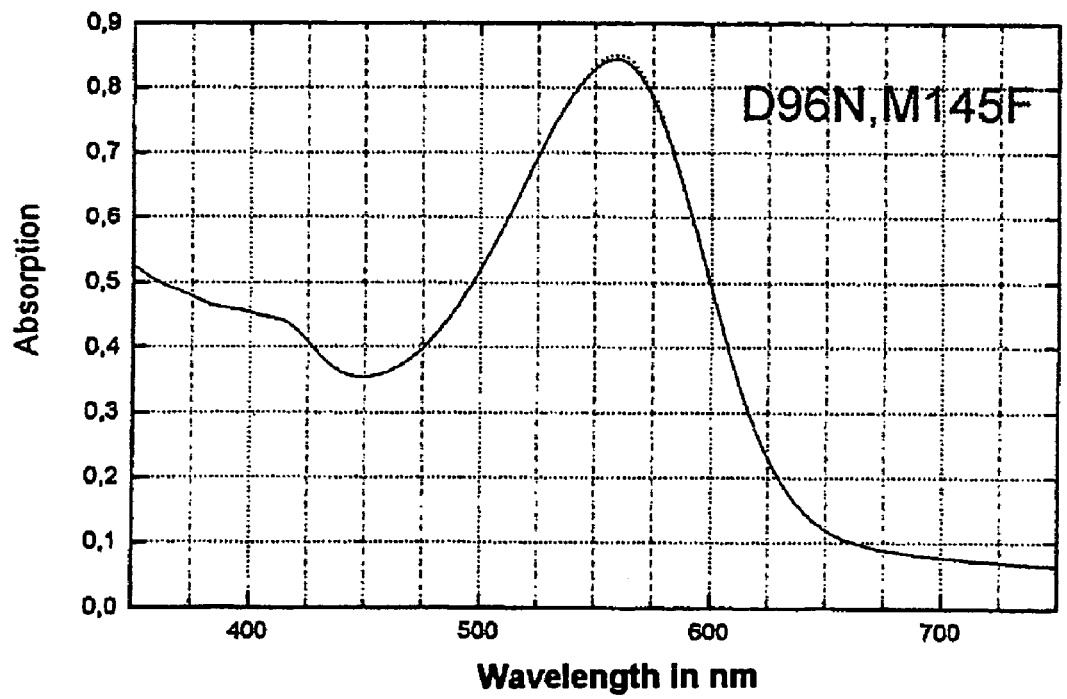

FIG. 1H shows the retinal protein according to the invention having the double mutation D96N-M145F. In the dark-adapted state, this double mutant achieves an all-trans content of 66%; the absorption maximum is 560 nm for both the light-adapted and the dark-adapted retinal protein.

EXAMPLE 1

Producing a Photochromic Composition

In order to produce a photochromic composition, the individual proton-translocating retinal proteins are firstly isolated, either from natural halobacterium populations or recombinantly by transforming *Halobacterium salinarum* (Cline & Doolittle, J. Bact. 169, 1341-1344, 1987) following site-specific mutagenesis of the bacteriorhodopsin gene (Dunn et al., Proc. Natl. Acad. Sc., USA 78, 6744-6748). Known methods are used to isolate and purify the purple membrane of the transformed halobacteria (Oesterhelt & Stoeckenius, Meth. Enzym. 31, 667-678, 1974). The method described in German patent application 199 45 798.0 can be used for isolating bacteriorhodopsin on a large scale.

EXAMPLE 2

Fixing the Photochromic Composition on a Surface

The photochromic composition according to the invention can, for example, be incorporated physically into a matrix material. Specifically, 10 mg of purple membrane, containing bacteriorhodopsin-D96N/M145F, for example, are suspended uniformly in 4 ml of a UV-curing dye (IFS 3000, from Schmitt) and applied to the document which requires security. After the document which has been labeled in this way has been subjected to UV illumination (in accordance with the manufacturer's instructions), the purple membrane particles are located in the cured plastic.

EXAMPLE 3

Using Various Methods to Apply the Photochromic Composition

Screen Printing

The principle of screen printing is porous printing, in a similar manner to a stenciling technique. The printing block consists of a screen fabric which is provided with a dye-impermeable barrier layer. The printing motif can be chosen as desired. The printing is effected by the dye-filled screen being scraped off using a doctor blade. In connection with this, the dye is transferred to the underlying substrate. In order to prepare a screen printing dye, 100 mg of purple membrane/ml are stirred overnight into a 7.2% solution of PVA (Mowiol type 56-98). When the rheological properties correspond to those of a standard sample, the mixture which is obtained can be printed using a conventional screen printing machine.

Offset Printing 1 mg of purple membrane is stirred, at 50° C., into 5 ml of a dye without pigment (from Schmitt, UFO1). The mixture which is obtained in this way can be printed using a conventional offset technique.

EXAMPLE 4

Producing an Abrasion-Resistant Security Feature

The photochromic composition can be made abrasion-resistant by, for example, using a hot-laminating appliance (GPM, Mylam 9) to laminate the proton-translocating retinal protein-coated documents in a film pocket of the GHQ-120TR type at a temperature of from 90 to 140° C.

EXAMPLE 5

Increasing the UV Resistance of the Security Feature

In order to increase the UV resistance of the security feature according to the invention, a UV absorber, or a derivative thereof, is added to the photochromic composition at a concentration of from 1 to 30%, preferably of from 3 to 10%, w/w. Preferred UV absorbers are benzophenone, hydroxynaphthoquinone, phenylbenzoxazole, cinnamic esters, sulfonamide and aminobenzoic esters.

The invention claimed is:

1. A photochromic composition comprising:
   (i) a proton-translocating retinal protein that is a mutein of a *Halobacterium salinarium* bacteriorhodopsin, which exhibits a retarded photocycle (type 1 mutation) and whose all-trans retinal contents in the light-adapted and dark-adapted states do not differ from each other by more than 10% (type 2 mutation), wherein said muteins comprises SEQ ID NO:1 except for one or more amino acid substitutions at a position selected from the group consisting of D38, D102, and D104 (type 1 mutation) and one or more amino acid substitutions at a position selected from the group consisting of V49, A53, L93, M118, G122, S141, and M145 (type 2 mutation);
   (ii) at least one additive selected from a stabilizer, a foam formation-diminishing additive, a UV light-absorbing additive and a buffering substance; and
   (iii) at least one additional component selected from glycerol, an organic polymer and an organic solvent.

2. The photochromic composition of claim 1 wherein the retinal protein is present in the form of a purple membrane.

3. A photochromic composition comprising:
   (i) a proton-translocating retinal protein that is a mutein of a *Halobacterium salinarium* bacteriorhodopsin, SEQ ID NO:1, which exhibits a retarded photocycle (type 1 mutation) and whose all-trans retinal contents in the light-adapted and dark-adapted states do not differ from each other by more than 10% (type 2 mutation), wherein said mutein comprises SEQ ID NO:1 except for the amino acid substitutions D96N (type 1 mutation) and M145F (type 2 mutation);
   (ii) at least one additive selected from a stabilizer, a foam formation-diminishing additive, a UV light-absorbing additive and a buffering substance; and
   (iii) at least one additional component selected from glycerol, an organic polymer and an organic solvent.

4. The photochromic composition of claim 3 wherein the retinal protein is present in the form of a purple membrane.

5. The photochromic composition of claim 1 wherein the proton-translocating retinal protein exhibits a retinal isomer composition of at least 60% all-trans retinal in both the light-adapted and dark-adapted states.

6. The photochromic composition of claim 2 wherein the density of the purple membrane is between 1.10 and 1.20 g/cm$^3$.

7. The photochromic composition of claim 6 wherein the density of the purple membrane is from 1.175 to 1.185 g/cm$^3$.

8. The photochromic composition of claim 3 wherein the proton-translocating retinal protein exhibits a retinal isomer composition of at least 60% all-trans retinal in both the light-adapted and dark-adapted states.

9. The photochromic composition of claim 4 wherein the density of the purple membrane is between 1.10 and 1.20 g/cm$^3$.

10. The photochromic composition of claim 9 wherein the density of the purple membrane is from 1.175 to 1.185 g/cm$^3$.

* * * * *

UNITED STATES PATENT AND TRADEMARK OFFICE
CERTIFICATE OF CORRECTION

| | | |
|---|---|---|
| PATENT NO. | : 7,939,220 B2 | Page 1 of 1 |
| APPLICATION NO. | : 10/343318 | |
| DATED | : May 10, 2011 | |
| INVENTOR(S) | : Dieter Oesterhelt et al. | |

It is certified that error appears in the above-identified patent and that said Letters Patent is hereby corrected as shown below:

Column 11, Line 8, Claim 1:
"more than 10% (type 2 mutation), wherein said muteins" should read, --more than 10% (type 2 mutation), wherein said mutein--.

Signed and Sealed this
Twentieth Day of December, 2011

David J. Kappos
*Director of the United States Patent and Trademark Office*